(12) United States Patent
Keith et al.

(10) Patent No.: US 6,805,866 B2
(45) Date of Patent: Oct. 19, 2004

(54) ORAL SUPPLEMENT COMPOSITION CONTAINING A PLURALITY OF MUSHROOM STRAINS

(75) Inventors: Alec D. Keith, Hilo, HI (US); Kelly N. Gaisford, Baizman, MT (US); Andrew H. Miller, San Francisco, CA (US)

(73) Assignee: Gaisford and Miller, Inc., Burlingame, CA (US)

( * ) Notice: Subject to any disclaimer, the term of this patent is extended or adjusted under 35 U.S.C. 154(b) by 0 days.

(21) Appl. No.: 10/252,743

(22) Filed: Sep. 23, 2002

(65) Prior Publication Data

US 2003/0133946 A1 Jul. 17, 2003

Related U.S. Application Data

(60) Provisional application No. 60/324,163, filed on Sep. 21, 2001.

(51) Int. Cl.[7] .................................................. A61K 35/84
(52) U.S. Cl. .................................... 424/195.15; 514/885
(58) Field of Search ...................... 424/195.15; 514/885

(56) References Cited

U.S. PATENT DOCUMENTS

| | | | |
|---|---|---|---|
| 5,997,875 A | * | 12/1999 | Zhou et al. |
| 6,106,867 A | * | 8/2000 | Mishima et al. |
| 6,277,396 B1 | * | 8/2001 | Dente |
| 6,468,541 B2 | * | 10/2002 | Lam |
| 2002/0164352 A1 | * | 11/2002 | Donatini |

FOREIGN PATENT DOCUMENTS

| | | | |
|---|---|---|---|
| CN | 1223135 | * | 7/1999 |
| JP | 53109913 | * | 9/1978 |

OTHER PUBLICATIONS

Marca Pharma Intl., MycoSurge® Liposome Spray, USA.
Mycoherb, Inc., Myco–Forte™, USA.

* cited by examiner

*Primary Examiner*—Christopher R. Tate
(74) *Attorney, Agent, or Firm*—Webb Ziesenheim Logsdon Orkin & Hanson, P.C.

(57) ABSTRACT

An oral supplement composition and method of making and using it, in which a combination of fourteen different specialized mushroom species, each of which has its own unique immunomodulatory properties, demonstrate enhancement of the immune system. When taken together, the combination of mushroom species exert a potentiated, synergistic effect that enhances immune function greater than the sum of each mushroom species' immunoenhancing influence. The oral supplement can be prepared into a variety of dosage forms, such as capsules, caplets, tablets, pills, dispersions, suspensions, solution, powders, teas, or syrup concentrates, and can be packaged in bottles or other packaging for sale.

27 Claims, No Drawings

ORAL SUPPLEMENT COMPOSITION CONTAINING A PLURALITY OF MUSHROOM STRAINS

CROSS REFERENCE TO RELATED APPLICATIONS

This application claims the benefit of U.S. Provisional Patent Application No. 60/324,163, filed Sep. 21, 2001, which is incorporated herein by reference.

BACKGROUND OF THE INVENTION

1. Field of the Invention

The present invention relates to an oral supplement composition and to a process for the production of the same. More particularly, fourteen different species of mushrooms are disclosed that exert enhanced immune function when taken together as a daily supplement.

2. Description of Related Art

The immune system is the body's basic protection and serves as both its essential mechanism for healing and its defense against premature aging. In general, it is believed that foodstuffs such as mushrooms, garlic, ginseng, American aloe and the like are effective in the promotion of human health, typically by enhancing immune function. It is well known there are many vitamins and minerals, essential fatty acids, proteins and carbohydrates which are required to sustain immune function. Recently the inadequate consumption of vitamins, minerals and essential-unsaturated fatty acids has been linked to various diseases, particularly those diseases of aging such as arthritis and cancer as well as others. A number of naturally-occurring ingredients in substances not normally included in the diet are known to inhibit or to reduce the growth of tumor cells, which suggests their immune-enhancing effect. Some examples of these items include herbs, edible fungus, e.g. mushrooms and antioxidants from natural raw sources such as grape seed or the Merritime pine bark.

Indeed, various mushroom species have been employed for centuries in Asian medicine, and their role in supporting immune function is currently being investigated in the scientific community. All plants produce certain kinds of sugars that are a source of energy and that form the cell walls in some plants. Some of the complex sugars in mushrooms are called alpha and beta glucans and are the focus of studies concerning their effects on the human immune system. Beta glucans are not produced naturally in humans, and must therefore come from plant and animal sources. Maitake mushrooms, for example, are exceptionally high in beta glucans, while shiitake mushrooms have high concentrations of alpha glucans.

Oral nutraceuticals have become very popular in recent years as research uncovers those specific compounds contained in food that have immunomodulatory effects. Thus, there is a continuing need for an oral supplement that exerts enhancement of the immune system in new and unexpected ways.

SUMMARY OF THE INVENTION

Accordingly, it is the object of the present invention to provide an oral supplement that contains a novel composition of mushroom species, which species have been shown to enhance immune function via bio-directed immunity. The oral supplement composition of the invention comprises a unique blend of fourteen different mushroom (fungi) species, each having its own properties that have been shown to have beneficial effects on the immune system. Moreover, when taken together, the combination of mushroom species exerts a potentiated, synergistic effect that boosts immune function to an extent greater than the sum of each mushroom species' immunomodulatory effect.

The oral supplement can be prepared into a variety of dosage forms, such as capsules, caplets, tablets, pills, dispersions, suspensions, solution, powders, teas, or syrup concentrates, and can be packaged in bottles or other packaging for sale. The advantages of such an oral composition will be more fully apparent in view of the following detailed description.

DESCRIPTION OF THE PREFERRED EMBODIMENT

The novel composition of the present invention is a nutraceutical created as an oral supplement composition containing a specialized blend of fourteen different mushroom (fungi) species that support and enhance the body's natural defenses via bio-directed immunity. The oral supplement provides a unique combination of natural organic compounds, based on extensive research in mushroom science, that includes rare varieties and specialized mushroom species, each having it own properties, some of which are found naturally only in hard-to-access regions, such as tropical rainforests and other remote areas of the world. For instance, *Ganoderma lucidum* has been traditionally known and used in oriental medicine for its antitumor effects but is unfamiliar and difficult to find in the United States.

The different specialized mushroom species of the present invention are grown in Hawaii under laboratory conditions for consistent results. Following is a list of the fourteen species of mushrooms and their active ingredient weight percentages: *Cordyceps sinensis*: 6% to 14%, more preferably 8% to 12%, most preferably 10%; *Agaricus blazei*: 4% to 12%, more preferably 6% to 10%, most preferably 8%; *Grifola frondosus*: 4% to 12%, more preferably 6% to 10%, most preferably 8%; *Ganoderma lucidum*: 4% to 12%, more preferably 6% to 10%, most preferably 8%; *Trametes versicolor*: 4% to 12%, more preferably 6% to 10%, most preferably 8%; *Lentinula edodes*: 4% to 12%, more preferably 6% to 10%, most preferably 8%; *Hericium erinaceus*: 4% to 12%, more preferably 6% to 10%, most preferably 8%; *Tremella mesenterica*: 2% to 10%, more preferably 4% to 8%, most preferably 6%; *Phellinus linteus*: 2% to 10%, more preferably 4% to 8%, most preferably 6%; *Pleurotus tuber-regium*: 2% to 10%, more preferably 4% to 8%, most preferably 6%; *Pleurotus ostreatus*: 2% to 10%, more preferably 4% to 8%, most preferably 6%; *Inonotus obliquus*: 2% to 10%, more preferably 4% to 8%, most preferably 6%; *Lepiota procera*: 2% to 10%, more preferably 4% to 8%, most preferably 6%; and *Flammulina velutipes*: 2% to 10%, more preferably 4% to 8%, most preferably 6%.

The fourteen mushroom species are grown under axenic (meaning only one life form) conditions in the vegetative state and on a sterile substrate of organic whole grain. The optimal growing temperature is between 60° C. and 70° C. After harvesting, each mushroom species is individually dried (to a moisture content less than 5%). The dried mushroom is then formed into a powder and mixed with the other similarly prepared thirteen mushroom species to form an admixture. The admixture is ground to between 60 and 80 mesh and autoclave sterilized. After sterilization, the admixture can be prepared into dosage forms that include, without limitation, capsules, caplets, tablets, pills, dispersions, suspensions, solution, powders, teas, or syrup concentrates.

The final product can then be packaged in bottles or other packaging for sale. When the final product is provided in capsule form, it also typically contains up to five parts by weight of the inactive ingredient magnesium stearate encapsulated in a vegetarian cellulose derivative, such as hydroxypropyl methylcellulose. When the final product is packaged as tablet, it also typically contains inactive ingredients, such as up to 2.5 parts by weight of acacia-based gum and up to 2.5 parts by weight of silicon dioxide. Alternative standard pharmaceutical ingredients may be substituted for the cellulose derivates, magnesium stearate, acacia-based gum and silicon dioxide according to the ordinary skill in the pharmaceutical arts.

Mushrooms are in the fungi phylum and have complex life cycles containing both a vegetative and a sexual cycle. During the sexual cycle the typical mushroom-shaped structure is produced containing spores. The spores germinate and grow producing 1 N hyphae. Later, opposite mating types of germ hyphae will fuse and produce a 2 N structure that is then in the vegetative growth phase. The vegetative growth continues until some great stress occurs interfering with their growth. This stressful condition induces the fungus (mushroom) to enter the sexual phase.

It has become apparent that different mushroom species vary substantially in their respective chemical fingerprints, and each species chosen for bio-directed immunity has unique chemical and immunomodulatory properties. Each of the mushroom species has a unique polysaccharide fraction that has been shown to have beneficial effects on the immune system. The purpose of preparing a cocktail of fourteen different specialized mushroom species is to maximize the chemical diversity of the mixture. Because different naturally occurring chemicals promote immunity in different ways, the fourteen mushroom species composition is better than any one or any lesser number of species. Indeed, it is the unique combinations of the enumerated components which give this oral supplement its potency for enhancing immune function. Thus, when taken together, the fourteen organically-grown, scientifically optimized specialized mushroom species exert a potentiated, synergistic effect that enhances immune function greater than the sum of each mushroom species' immunomodulatory influence.

EXAMPLE 1

The following composition of mushroom species was used to prepare a 500 mg oral supplement packaged in capsule form. Inactive ingredients consisted of magnesium stearate and hydroxypropyl methylcellulose. The recommended daily dose of two capsules were taken separately during the day for maximum absorption.

| Ingredient | Amount (% total weight active ingredients) |
|---|---|
| Cordyceps sinensis | 10 |
| Agaricus blazei | 8 |
| Grifola frondosus | 8 |
| Ganoderma lucidum | 8 |
| Trametes versicolor | 8 |
| Lentinula edodes | 8 |
| Hericium erinaceus | 8 |
| Tremella mesenterica | 6 |
| Phellinus linteus | 6 |
| Pleurotus tuber-regium | 6 |
| Pleurotus ostreatus | 6 |
| Inonotus obliquus | 6 |
| Lepiota procera | 6 |
| Flammulina velutipes | 6 |

EXAMPLE 2

The following composition of mushroom species can be prepared as a 500 mg oral supplement packaged in tablet form. Inactive ingredients are acacia-based gum and silicon dioxide. A recommended daily dose of two tablets should be taken separately during the day for maximum absorption.

| Ingredient | Amount (% total weight active ingredients) |
|---|---|
| Cordyceps sinensis | 14 |
| Agaricus blazei | 4 |
| Grifola frondosus | 12 |
| Ganoderma lucidum | 4 |
| Trametes versicolor | 12 |
| Lentinula edodes | 4 |
| Hericium erinaceus | 12 |
| Tremella mesenterica | 2 |
| Phellinus linteus | 10 |
| Pleurotus tuber-regium | 2 |
| Pleurotus ostreatus | 10 |
| Inonotus obliquus | 2 |
| Lepiota procera | 10 |
| Flammulina velutipes | 2 |

EXAMPLE 3

The following composition of mushroom species can be prepared as a 500 mg oral supplement packaged in tablet form. Inactive ingredients are acacia-based gum and silicon dioxide. A recommended daily dose of two tablets should be taken separately during the day for maximum absorption.

| Ingredient | Amount (% total weight active ingredients) |
|---|---|
| Cordyceps sinensis | 6 |
| Agaricus blazei | 12 |
| Grifola frondosus | 4 |
| Ganoderma lucidum | 12 |
| Trametes versicolor | 4 |
| Lentinula edodes | 12 |
| Hericium erinaceus | 4 |
| Tremella mesenterica | 10 |
| Phellinus linteus | 2 |
| Pleurotus tuber-regium | 10 |
| Pleurotus ostreatus | 2 |
| Inonotus obliquus | 10 |
| Lepiota procera | 2 |
| Flammulina velutipes | 10 |

EXAMPLE 4

The following composition of mushroom species can be prepared as a 500 mg oral supplement packaged in caplet form. Inactive ingredients are acacia-based gum and silicon dioxide. A recommended daily dose of two tablets should be taken separately during the day for maximum absorption.

| Ingredient | Amount (% total weight active ingredients) |
| --- | --- |
| Cordyceps sinensis | 12 |
| Agaricus blazei | 6 |
| Grifola frondosus | 10 |
| Ganoderma lucidum | 6 |
| Trametes versicolor | 10 |
| Lentinula edodes | 6 |
| Hericium erinaceus | 10 |
| Tremella mesenterica | 4 |
| Phellinus linteus | 8 |
| Pleurotus tuber-regium | 4 |
| Pleurotus ostreatus | 8 |
| Inonotus obliquus | 4 |
| Lepiota procera | 8 |
| Flammulina velutipes | 4 |

EXAMPLE 5

The following composition of mushroom species can be prepared as a 500 mg oral supplement packaged in caplet form. Inactive ingredients are acacia-based gum and silicon dioxide. A recommended daily dose of two tablets should be taken separately during the day for maximum absorption.

| Ingredient | Amount (% total weight active ingredients) |
| --- | --- |
| Cordyceps sinensis | 8 |
| Agaricus blazei | 10 |
| Grifola frondosus | 6 |
| Ganoderma lucidum | 10 |
| Trametes versicolor | 6 |
| Lentinula edodes | 10 |
| Hericium erinaceus | 6 |
| Tremella mesenterica | 8 |
| Phellinus linteus | 4 |
| Pleurotus tuber-regium | 8 |
| Pleurotus ostreatus | 4 |
| Inonotus obliquus | 8 |
| Lepiota procera | 4 |
| Flammulina velutipes | 8 |

The present invention has been described with reference to specific details of particular embodiments thereof. It is not intended that such details be regarded as limitations upon the scope of the invention except insofar as and to the extent that they are included in the accompanying claims.

The invention claimed is:

1. An oral supplement composition for use in enhancing the immune system of an animal or human, comprising:
   a. an orally ingestible carrier or diluent; and
   b. fourteen different mushroom ingredients according to the following species and amounts (by weight):
      1) 6% to 14% of *Cordyceps sinensis*,
      2) 4% to 12% of *Agaricus blazei*,
      3) 4% to 12% of *Grifola frondosus*,
      4) 4% to 12% of *Ganoderma lucidum*,
      5) 4% to 12% of *Trametes versicolor*,
      6) 4% to 12% of *Lentinula edodes*,
      7) 4% to 12% of *Hericium erinaceus*,
      8) 2% to 10% of *Tremella mesenterica*,
      9) 2% to 10% of *Phellinus linteus*,
      10) 2% to 10% of *Pleurotus tuber-regium*,
      11) 2% to 10% of *Pleurotus ostreatus*,
      12) 2% to 10% of *Inonotus obliquus*,
      13) 2% to 10% of *Lepiota procera*, and
      14) 2% to 10% of *Flammulina velutipes*.

2. The oral supplement composition according to claim 1, wherein the fourteen mushroom ingredients are present according to the following species and amounts:
   1) 8% to 12% of *Cordyceps sinensis*,
   2) 6% to 10% of *Agaricus blazei*,
   3) 6% to 10% of *Grifola frondosus*,
   4) 6% to 10% of *Ganoderma lucidum*,
   5) 6% to 10% of *Trametes versicolor*,
   6) 6% to 10% of *Lentinula edodes*,
   7) 6% to 10% of *Hericium erinaceus*,
   8) 4% to 8% of *Tremella mesenterica*,
   9) 4% to 8% of *Phellinus linteus*,
   10) 4% to 8% of *Pleurotus tuber-regium*,
   11) 4% to 8% of *Pleurotus ostreatus*,
   12) 4% to 8% of *Inonotus obliquus*,
   13) 4% to 8% of *Lepiota procera*, and
   14) 4% to 8% of *Flammulina velutipes*.

3. The oral supplement composition according to claim 2, wherein the fourteen mushroom ingredients are present according to the following species and amounts:
   1) 10% of *Cordyceps sinensis*,
   2) 8% of *Agaricus blazei*,
   3) 8% of *Grifola frondosus*,
   4) 8% of *Ganoderma lucidum*,
   5) 8% of *Trametes versicolor*,
   6) 8% of *Lentinula edodes*,
   7) 8% of *Hericium erinaceus*,
   8) 6% of *Tremella mesenterica*,
   9) 6% of *Phellinus linteus*,
   10) 6% of *Pleurotus tuber-regium*,
   11) 6% of *Pleurotus ostreatus*,
   12) 6% of *Inonotus obliquus*,
   13) 6% of *Lepiota procera*, and
   14) 6% of *Flammulina velutipes*.

4. The oral supplement composition according to claim 2, wherein the dosage form is selected from the group consisting of capsules, caplets, tablets, pill, dispersions, suspensions, solutions, powders, teas, and syrup concentrates.

5. The oral supplement composition according to claim 2, wherein said capsules contain up to 5 parts by weight of the inactive ingredient magnesium stearate in a vegetarian excipient of hydroxypropyl methylcellulose.

6. The oral supplement composition according to claim 2, wherein said tablets contain inactive ingredients of up to 2.5 parts by weight of acacia-based gum and up to 2.5 parts by weight of silicon dioxide.

7. The oral supplement composition according to claim 2, wherein said mushroom species are grown on a sterile substrate of organic whole grain.

8. The oral supplement composition according to claim 2, wherein said mushroom species are grown at a temperature between 60° C. and 70° C.

9. The oral supplement composition according to claim 2, wherein each said mushroom species is individually dried to a moisture content less than 5%.

10. The oral supplement composition according to claim 2, wherein each said mushroom species is formed into a powder.

11. The oral supplement composition according to claim 2, wherein each mushroom species is mixed with thirteen other mushroom species to form an admixture.

12. The oral supplement composition according to claim 11, wherein said admixture is ground to between 60 and 80 mesh.

13. The oral supplement composition according to claim 12, wherein said admixture is autoclave sterilized.

14. A method to prepare an oral supplement composition for use in enhancing the immune system of an animal or human, comprising:
   a. combining fourteen different powdered mushroom ingredients to form an admixture according to the following species and amounts (by weight):
      1) 6% to 14% of *Cordyceps sinensis*,
      2) 4% to 12% of *Agaricus blazei*,
      3) 4% to 12% of *Grifola frondosus*,
      4) 4% to 12% of *Ganoderma lucidum*,
      5) 4% to 12% of *Trametes versicolor*,
      6) 4% to 12% of *Lentinula edodes*,
      7) 4% to 12% of *Hericium erinaceus*,
      8) 2% to 10% of *Tremella mesenterica*,
      9) 2% to 10% of *Phellinus linteus*,
      10) 2% to 10% of *Pleurotus tuber-regium*,
      11) 2% to 10% of *Pleurotus ostreatus*,
      12) 2% to 10% of *Inonotus obliquus*,
      13) 2% to 10% of *Lepiota procera*, and
      14) 2% to 10% of *Flammulina velutipes*.
   b. sterilizing said admixture in an autoclave; and
   c. packaging said admixture into a dosage form.

15. The method according to claim 14, wherein the fourteen powdered mushroom ingredients are present according to the following species and amounts:
   1) 8% to 12% of *Cordyceps sinensis*,
   2) 6% to 10% of *Agaricus blazei*,
   3) 6% to 10% of *Grifola frondosus*,
   4) 6% to 10% of *Ganoderma lucidum*,
   5) 6% to 10% of *Trametes versicolor*,
   6) 6% to 10% of *Lentinula edodes*,
   7) 6% to 10% of *Hericium erinaceus*,
   8) 4% to 8% of *Tremella mesenterica*,
   9) 4% to 8% of *Phellinus linteus*,
   10) 4% to 8% of *Pleurotus tuber-regium*,
   11) 4% to 8% of *Pleurotus ostreatus*,
   12) 4% to 8% of *Inonotus obliquus*,
   13) 4% to 8% of *Lepiota procera*, and
   14) 4% to 8% of *Flammulina velutipes*.

16. The method according to claim 15, wherein the fourteen powdered mushroom ingredients are present according to the following species and amounts:
   1) 10% of *Cordyceps sinensis*,
   2) 8% of *Agaricus blazei*,
   3) 8% of *Grifola frondosus*,
   4) 8% of *Ganoderma lucidum*,
   5) 8% of *Trametes versicolor*,
   6) 8% of *Lentinula edodes*,
   7) 8% of *Hericium erinaceus*,
   8) 6% of *Tremella mesenterica*,
   9) 6% of *Phellinus linteus*,
   10) 6% of *Pleurotus tuber-regium*,
   11) 6% of *Pleurotus ostreatus*,
   12) 6% of *Inonotus obliquus*,
   13) 6% of *Lepiota procera*, and
   14) 6% of *Flammulina velutipes*.

17. The method according to claim 15, wherein said dosage form is selected from the group consisting of capsules, caplets, tablets, pill, dispersions, suspensions, solutions, powders, teas, and syrup concentrates.

18. The method according to claim 15, wherein said capsules contain up to 5 parts by weight of the inactive ingredient magnesium stearate in a vegetarian excipient of hydroxypropyl methylcellulose.

19. The method according to claim 15, wherein said tablets contain inactive ingredients of up to 2.5 parts by weight of acacia-based gum and up to 2.5 parts by weight of silicon dioxide.

20. The method according to claim 15, wherein said mushroom species are grown at a temperature between 60° C. and 70° C.

21. A method for enhancing the immune system in an animal or human in which such enhancement is indicated, comprising:
   a. administering in unit dosage form a combination of fourteen different powdered mushroom ingredients according to the following species and amounts (by weight):
      1) 6% to 14% of *Cordyceps sinensis*,
      2) 4% to 12% of *Agaricus blazei*,
      3) 4% to 12% of *Grifola frondosus*,
      4) 4% to 12% of *Ganoderma lucidum*,
      5) 4% to 12% of *Trametes versicolor*,
      6) 4% to 12% of *Lentinula edodes*,
      7) 4% to 12% of *Hericium erinaceus*,
      8) 2% to 10% of *Tremella mesenterica*,
      9) 2% to 10% of *Phellinus linteus*,
      10) 2% to 10% of *Pleurotus tuber-regium*,
      11) 2% to 10% of *Pleurotus ostreatus*,
      12) 2% to 10% of *Inonotus obliquus*,
      13) 2% to 10% of *Lepiota procera*, and
      14) 2% to 10% of *Flammulina velutipes*.

22. The method according to claim 21, wherein the fourteen powdered mushroom ingredients are present according to the following species and amounts:
   1) 8% to 12% of *Cordyceps sinensis*,
   2) 6% to 10% of *Agaricus blazei*,
   3) 6% to 10% of *Grifola frondosus*,
   4) 6% to 10% of *Ganoderma lucidum*,
   5) 6% to 10% of *Trametes versicolor*,
   6) 6% to 10% of *Lentinula edodes*,
   7) 6% to 10% of *Hericium erinaceus*,
   8) 4% to 8% of *Tremella mesenterica*,
   9) 4% to 8% of *Phellinus linteus*,
   10) 4% to 8% of *Pleurotus tuber-regium*,
   11) 4% to 8% of *Pleurotus ostreatus*,
   12) 4% to 8% of *Inonotus obliquus*,
   13) 4% to 8% of *Lepiota procera*, and
   14) 4% to 8% of *Flammulina velutipes*.

23. The method according to claim 22, wherein the fourteen powdered mushroom ingredients are present according to the following species and amounts:
   1) 10% of *Cordyceps sinensis*,
   2) 8% of *Agaricus blazei*,
   3) 8% of *Grifola frondosus*,
   4) 8% of *Ganoderma lucidum*,
   5) 8% of *Trametes versicolor*,
   6) 8% of *Lentinula edodes*,
   7) 8% of *Hericium erinaceus*,
   8) 6% of *Tremella mesenterica*,
   9) 6% of *Phellinus linteus*, 10) 6% of *Pleurotus tuber-regium,*
11) 6% of *Pleurotus ostreatus,*
12) 6% of *Inonotus obliquus,*
13) 6% of *Lepiota procera, and*
14) 6% of *Flammulina velutipes.*

24. The method according to claim 22, wherein said dosage form is selected from the group consisting of capsules, caplets, tablets, pill, dispersions, suspensions, solutions, powders, teas, and syrup concentrates.

25. The method according to claim 22, wherein said capsules contain up to 5 parts by weight of the inactive ingredient magnesium stearate in a vegetarian excipient of hydroxypropyl methylcellulose.

26. The method according to claim 22, wherein said tablets contain inactive ingredients of up to 2.5 parts by weight of acacia-based gum and up to 2.5 parts by weight of silicon dioxide.

27. The method according to claim 22, wherein said mushroom species are grown at a temperature between 60° C. and 70° C.

* * * * *

UNITED STATES PATENT AND TRADEMARK OFFICE
CERTIFICATE OF CORRECTION

PATENT NO. : 6,805,866 B2
DATED : October 19, 2004
INVENTOR(S) : Keith et al.

It is certified that error appears in the above-identified patent and that said Letters Patent is hereby corrected as shown below:

Title page,
Item [75], Inventors, "Kelly N. Gaisford, Baizman, MT" should read
-- Kelly W. Gaisford, Bozeman, MT --

Signed and Sealed this

Third Day of May, 2005

JON W. DUDAS
*Director of the United States Patent and Trademark Office*